US012642607B2

(12) United States Patent
Flakne et al.

(10) Patent No.: US 12,642,607 B2
(45) Date of Patent: Jun. 2, 2026

(54) ENERGIZED SUCTION AND IRRIGATION DEVICE FOR ROBOTIC SURGICAL SYSTEM

(71) Applicant: Cilag GmbH International, Zug (CH)

(72) Inventors: Kyle R. Flakne, Cincinnati, OH (US);
David C. Groene, Cincinnati, OH
(US); Laura A. Nye, Cincinnati, OH
(US); Kris E. Kallenberger,
Cincinnati, OH (US)

(73) Assignee: CILAG GMBH INTERNATIONAL,
Zug (CH)

( * ) Notice: Subject to any disclaimer, the term of this
patent is extended or adjusted under 35
U.S.C. 154(b) by 474 days.

(21) Appl. No.: 18/085,008

(22) Filed: Dec. 20, 2022

(65) Prior Publication Data

US 2024/0197414 A1 Jun. 20, 2024

(51) Int. Cl.
*A61B 34/30* (2016.01)
*A61B 18/00* (2006.01)
(Continued)

(52) U.S. Cl.
CPC .............. *A61B 34/30* (2016.02); *A61B 18/14*
(2013.01); *A61B 90/50* (2016.02);
(Continued)

(58) Field of Classification Search
CPC ......... A61B 34/30; A61B 90/50; A61B 18/14;
A61B 18/082; A61B 2018/00708;
(Continued)

(56) References Cited

U.S. PATENT DOCUMENTS 9,763,741 B2 9/2017 Alvarez et al.
10,166,082 B1 1/2019 Hariri et al.
(Continued)

FOREIGN PATENT DOCUMENTS

WO WO-2019140105 A1 * 7/2019 .......... A61B 1/0052
WO 2022/074647 A1 4/2022

OTHER PUBLICATIONS

International Search Report and Written Opinion dated Jul. 15, 2024
for Application No. PCT/IB2023/062874, 17 pages.
Invitation to Pay Additional Fees dated Jul. 15, 2024 for Application
No. PCT/IB2023/062874, 10 pages.

*Primary Examiner* — Beverly M Flanagan
(74) *Attorney, Agent, or Firm* — FBT Gibbons LLP

(57) ABSTRACT

A robotic surgical system includes a robotic arm and a
surgical instrument. The surgical instrument is configured to
connect with the robotic arm. The surgical instrument
includes a shaft assembly, an end effector, and an articulat-
able section. The shaft assembly projects distally from the
robotic arm along a longitudinal axis. The end effector
includes an electrode and at least one aperture. The electrode
is configured to apply electrosurgical energy to tissue. The
end effector has at least one aperture is configured to receive
a fluid or a vacuum therethrough for irrigating the tissue or
removing debris from the patient. The articulatable section
is disposed between the shaft assembly and the end effector.
The articulatable section is configured to deflect the end
effector between a straight configuration where the end
effector extends along the longitudinal axis and an articu-
lated configuration where the end effector is deflected from
the longitudinal axis.

20 Claims, 15 Drawing Sheets

(51) Int. Cl.

| | |
|---|---|
| *A61B 18/12* | (2006.01) |
| *A61B 18/14* | (2006.01) |
| *A61B 90/50* | (2016.01) |

(52) U.S. Cl.
CPC .............. *A61B 2018/00708* (2013.01); *A61B 2018/0072* (2013.01); *A61B 2018/1253* (2013.01); *A61B 2018/126* (2013.01); *A61B 2218/002* (2013.01); *A61B 2218/008* (2013.01)

(58) Field of Classification Search
CPC ...... A61B 2018/1253; A61B 2018/126; A61B 2018/00202; A61B 2018/1435; A61B 2218/002; A61B 2218/008
USPC .......................................................... 606/41
See application file for complete search history.

(56) References Cited

U.S. PATENT DOCUMENTS

| | | | |
|---|---|---|---|
| 10,464,209 B2 | 11/2019 | Ho et al. | |
| 10,667,875 B2 | 6/2020 | DeFonzo et al. | |
| 10,765,303 B2 | 9/2020 | Graetzel et al. | |
| 10,827,913 B2 | 11/2020 | Ummalaneni et al. | |
| 10,881,280 B2 | 1/2021 | Baez, Jr. | |
| 10,898,277 B2 | 1/2021 | Srinivasan et al. | |
| 11,058,493 B2 | 7/2021 | Rafii-Tari et al. | |
| 2005/0131390 A1 * | 6/2005 | Heinrich | A61B 17/07207 |
| | | | 606/1 |
| 2009/0326527 A1 | 12/2009 | Ocel et al. | |
| 2018/0147005 A1 | 5/2018 | Goshgarian et al. | |
| 2020/0237423 A1 | 7/2020 | Witte et al. | |
| 2022/0338927 A1 | 10/2022 | Rzeszutek et al. | |

* cited by examiner

CONTROL
CONSOLE

28

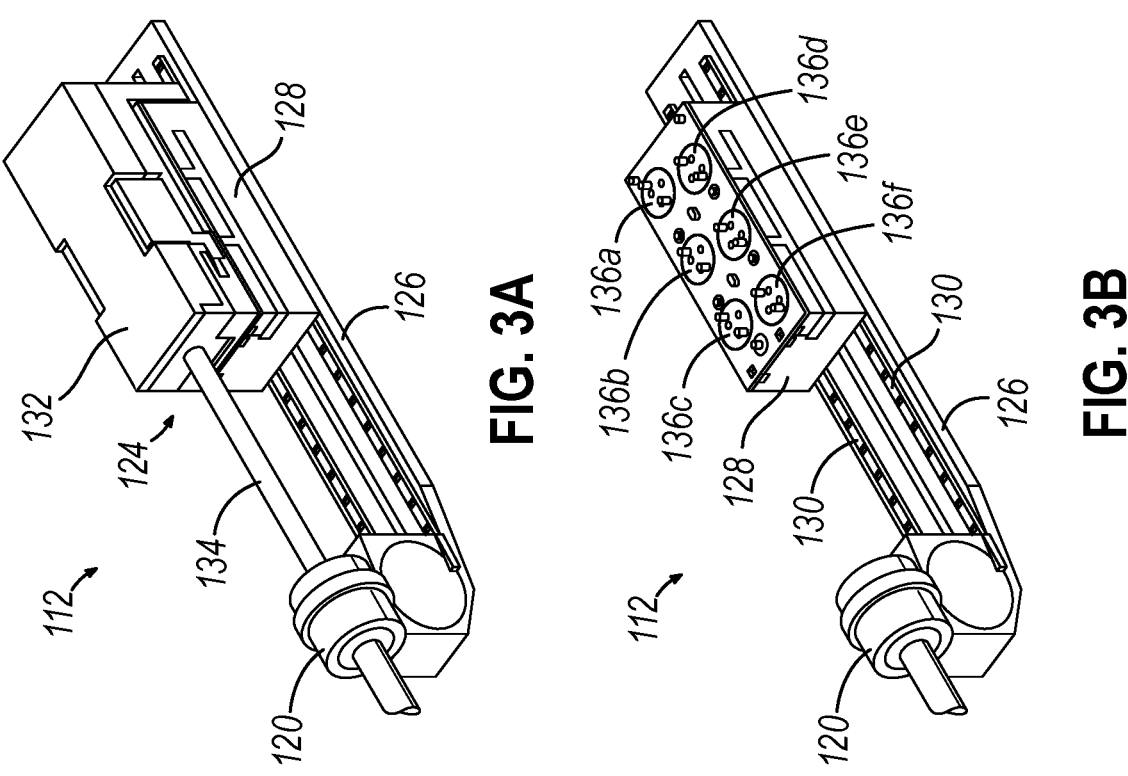
FIG. 3A
FIG. 3B
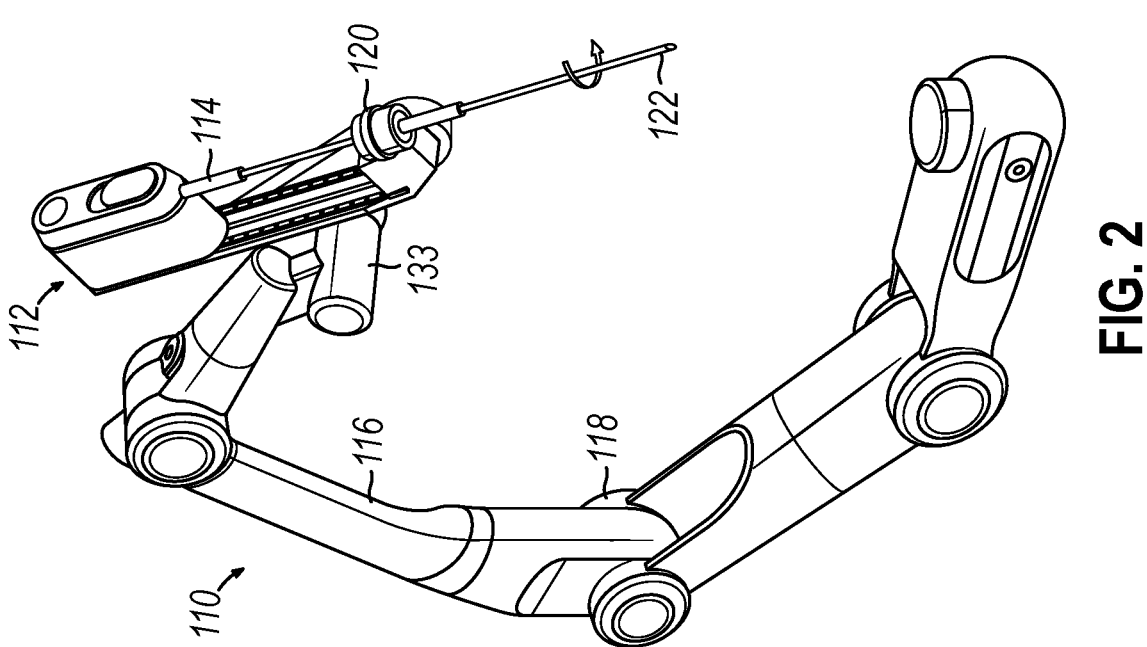
FIG. 2

ENERGIZED SUCTION AND IRRIGATION DEVICE FOR ROBOTIC SURGICAL SYSTEM

BACKGROUND

A variety of medical instruments may be used in procedures conducted by a medical professional operator, as well as applications in robotically assisted surgeries. In the case of robotically assisted surgery, the clinician may operate a master controller to remotely control the motion of such medical instruments at a surgical site. The controller may be separated from the patient by a significant distance (e.g., across the operating room, in a different room, or in a completely different building than the patient). Alternatively, a controller may be positioned quite near the patient in the operating room. Regardless, the controller may include one or more hand input devices (such as joysticks, exoskeletol gloves, master manipulators, or the like), which are coupled by a servo mechanism to the medical instrument. In some scenarios, a servo motor moves a manipulator supporting the medical instrument based on the clinician's manipulation of the hand input devices. During the medical procedure, the clinician may employ, via a robotic system, a variety of medical instruments including an ultrasonic blade, a surgical stapler, a tissue grasper, a needle driver, an electrosurgical cautery probes, etc. Each of these structures performs functions for the clinician, for example, cutting tissue, coagulating tissue, holding or driving a needle, grasping a blood vessel, dissecting tissue, or cauterizing tissue.

Examples of robotic systems are described in U.S. Pat. No. 9,763,741, entitled "System for Robotic-Assisted Endolumenal Surgery and Related Methods," issued Sep. 19, 2017, the disclosure of which is incorporated by reference herein, in its entirety; U.S. Pat. No. 10,464,209, entitled "Robotic System with Indication of Boundary for Robotic Arm," issued Nov. 5, 2019, the disclosure of which is incorporated by reference herein, in its entirety; U.S. Pat. No. 10,667,875, entitled "Systems and Techniques for Providing Multiple Perspectives During Medical Procedures," issued Jun. 2, 2020, the disclosure of which is incorporated by reference herein, in its entirety; U.S. Pat. No. 10,765,303, entitled "System and Method for Driving Medical Instrument," issued Sep. 8, 2020, the disclosure of which is incorporated by reference herein, in its entirety; U.S. Pat. No. 10,827,913, entitled "Systems and Methods for Displaying Estimated Location of Instrument," issued Nov. 10, 2020, the disclosure of which is incorporated by reference herein, in its entirety; U.S. Pat. No. 10,881,280, entitled "Manually and Robotically Controllable Medical Instruments," issued Jan. 5, 2021, the disclosure of which is incorporated by reference herein, in its entirety; U.S. Pat. No. 10,898,277, entitled "Systems and Methods for Registration of Location Sensors," issued Jan. 26, 2012, the disclosure of which is incorporated by reference herein, in its entirety; and U.S. Pat. No. 11,058,493, entitled "Robotic System Configured for Navigation Path Tracing," issued Jul. 13, 2021, the disclosure of which is incorporated by reference herein, in its entirety.

While several medical instruments, systems, and methods have been made and used, it is believed that no one prior to the inventors has made or used the invention described in the appended claims.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

FIG. 2 depicts a perspective view of an example of a robotic arm, an example of a tool drive, and a first example of a surgical instrument, each configured for use with the table-based robotic system of FIG. 1;

FIG. 3A depicts an enlarged schematic perspective view of the tool driver and the surgical instrument of FIG. 2;

FIG. 3B depicts a schematic perspective view of the tool driver similar to FIG. 3A, but with the surgical instrument removed to expose rotary drives;

DETAILED DESCRIPTION

I. Overview of Example of Robotic Surgical System

Aspects of the present disclosure may be integrated into a robotically-enabled medical system capable of performing a variety of medical procedures, including both minimally invasive, such as laparoscopy, and non-invasive, such as endoscopy, procedures. Among endoscopy procedures, the system may be capable of performing bronchoscopy, ureteroscopy, gastroscopy, etc.

In addition to performing the breadth of procedures, the system may provide additional benefits, such as enhanced imaging and guidance to assist the clinician. Additionally, the system may provide the clinician with the ability to perform the procedure from an ergonomic position without the need for awkward arm motions and positions. Still further, the system may provide the clinician with the ability to perform the procedure with improved ease of use such that one or more of the instruments of the system can be controlled by a single user.

Various embodiments will be described below in conjunction with the drawings for purposes of illustration. It should be appreciated that many other implementations of the disclosed concepts are possible, and various advantages can be achieved with the disclosed implementations. Headings are included herein for reference and to aid in locating various sections. These headings are not intended to limit the scope of the concepts described with respect thereto. Such concepts may have applicability throughout the entire specification.

A. Example of Robotic System Table

Figure 1:
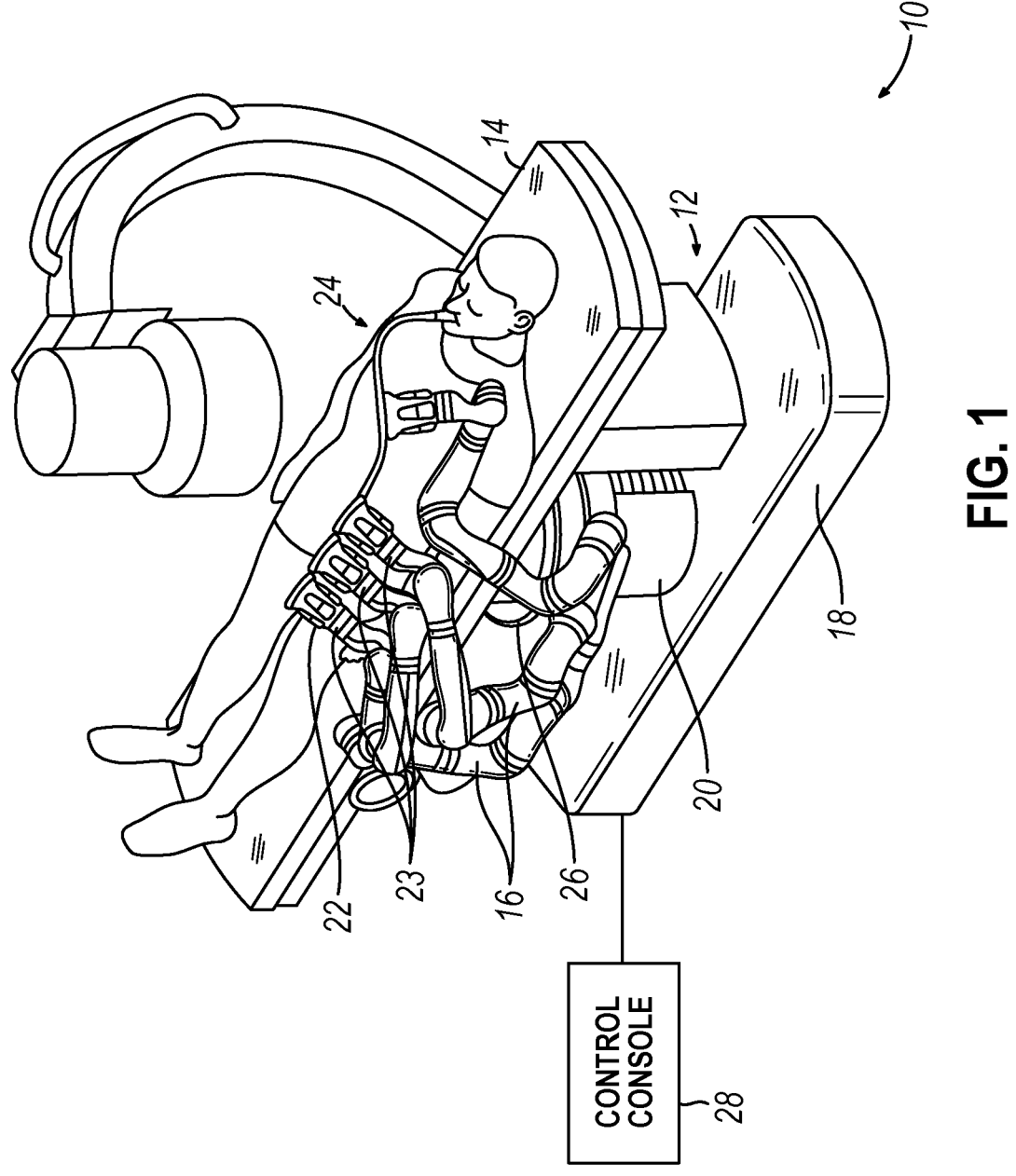
FIG. 1 depicts a perspective view of an example of a table-based robotic system that includes a control console and a plurality of robotic arms.

FIG. 1 illustrates an example of a robotic surgical system (10). Robotic surgical system (10) includes a support structure (12) for supporting a platform (14) (shown as a "table" or "bed") over the floor and one or more robotic arms (16). Support structure (12) includes a base (18) and a column (20). Column (20) structurally supports platform (14), and provides a path for vertical translation of the carriages. In some versions, a table base may stow and store robotic arms (16) when not in use. Column (20) of the present example also includes a ring-shaped carriage (26), from which robotic arms (16) are based. A control console (28) is coupled with robotic surgical system (10). While four robotic arms are shown, more or fewer robotic arms are envisioned.

Robotic arms (16) are shown as part of a table-mounted system, but in other configurations, robotic arms (16) may be mounted in a cart, ceiling or sidewall, or other suitable support surface. Robotic arms (16) are shown as extending from column (20) via carriage (26). However, robotic arms (16) may be coupled with robotic surgical system (10) using a variety of suitable structures. While robotic arms (16) are all shown as being positioned on one side of the patient in FIG. 1, other configurations may position robotic arms (16) on both sides of the patient, between the legs of the patient, and/or in any other suitable locations. Tool drivers (22) are positioned at distal ends (23) of robotic arms (16) in the present example. Tool drivers (22) are operable to manipulate one or more surgical instruments (24), as will be described in greater detail below.

B. Example of a Robotic Arm, Tool Drive, and Tool

FIG. 2 shows an example of a robotic arm (110), a tool driver (112), and a surgical instrument (114), which may be incorporated into robotic surgical system (10) in place of a robotic arm (16), a tool driver (22), and a surgical instrument (24) that are shown in FIG. 1. Additional examples of robotic arms, tool drivers, and surgical instruments are shown and described in U.S. Pat. No. 10,166,082, entitled "System and Method for Controlling a Robotic Wrist," issued Jan. 1, 2019, the disclosure of which is incorporated by reference herein, in its entirety.

As shown in FIG. 2, robotic arm (110) includes a plurality of links (116) and a plurality of joints (118) for actuating links (116) relative to one another. Tool driver (112) is attached to the distal end of robotic arm (110). Tool driver (112) includes a cannula (120) coupled to the end of tool driver (112), to receive and guide surgical instrument (114). Surgical instrument (114) may include an endoscope, a laparoscope, a stapler, graspers, an ultrasonic instrument, an RF electrosurgical instrument, or any other suitable kind of instrument. Surgical instrument (114) is inserted into the patient via cannula (120). The distal end of surgical instrument (114) includes an end effector (122). End effector (122) is configured to interact with the patient (e.g., providing visualization, stapling, grasping, ultrasonic cutting and/or sealing, electrosurgical cutting and/or sealing, etc.).

Joints (118) of robotic arm (110) may be actuated to selectively position and orient tool driver (112), which actuates the end effector (122) for robotic surgeries. Joints (118) may include various types, such as a pitch joint or a roll joint, which may substantially constrain the movement of the adjacent links (116) around certain axes relative to other links (116). Each joint (118) represents an independent degree of freedom available to robotic arm (110). A multitude of joints (118) result in a multitude of degrees of freedom, allowing for "redundant" degrees of freedom. Redundant degrees of freedom allow the robotic arms (110) to position their respective end effectors (122) at a specific position, orientation, and trajectory in space using different positions links (116) and angles of joints (118). This allows for the system to position and direct a surgical instrument (114) from a desired point in space while allowing the clinician to move joints (118) into a clinically advantageous position away from the patient to create greater access, while avoiding collisions of robotic arms (110).

FIGS. 3A and 3B show tool driver (112) with and without a tool driver adapter (124), which may also be referred to as a tool base. As shown in FIGS. 3A and 3B, tool driver (112) may include a stage (126) and a carriage (128). Stage (126) includes longitudinal tracks (130). Carriage (128) is slidingly engaged with longitudinal tracks (130). Stage (126) of tool driver (112) may be configured to couple to a distal end (133) of robotic arm (110) such that articulation of robotic arm (110) positions and/or orients tool driver (112) in space. Surgical instrument (114) includes a tool driver adapter (124) at a proximal end and, as noted above, end effector (122) at a distal end. Tool driver adapter (124) includes a handle (132) and a shaft assembly (134) that extends distally from handle (132).

Carriage (128) is configured to couple with tool driver adapter (124). Carriage (128) may drive a set of articulated movements of end effector (122) and/or otherwise actuate end effector (122), such as through a cable system or wires manipulated and controlled by actuated drives. Carriage (128) may include different configurations of actuated drives, including but not limited to motorized rotary axis drives. The plurality of rotary axis drives may be arranged in any suitable manner. As shown in FIG. 3B, carriage (128) of the present example includes six rotary drives (136a-f) arranged in two rows, extending longitudinally along the base of carriage (128). Rotary drives (136a-c) are arranged in a first row that is longitudinally offset from a second row in which rotary drives (136d-f) are arranged. This staggered arrangement of rotary drives (136a-f) may reduce the width of carriage (128) and thereby provide a more compact form factor for tool driver (112). However, rotary drives (136a-f) may be provided in any other suitable arrangement. More-over, any other suitable kind(s) of drive outputs may be provided by carriage (128), in addition to or in lieu of rotary drives (136a-f).

II. Examples of Surgical Instruments

A. Overview

Robotic surgical system (10) includes a limited number of robotic arms (16, 110) onto which scopes and other surgical instruments may be coupled. Given the space constraints of robotic laparoscopic instrumentation, there are competing demands for use of these limited number of robotic arms (16, 110). For example, a surgeon may not want to dedicate a robotic arm to a surgical instrument that provides only suction, only irrigation, or only electrosurgical energy. As a result, it is beneficial for a surgical instrument coupled with one of robotic arms (16, 110) to perform multiple functions during the course of a surgical procedure. Additionally, utilizing a surgical instrument that performs multiple functions reduces or eliminates surgical time associated with exchanging a first surgical instrument with a second surgical instrument providing a different function or capability.

B. Example of a Surgical Instrument

Figure 4:
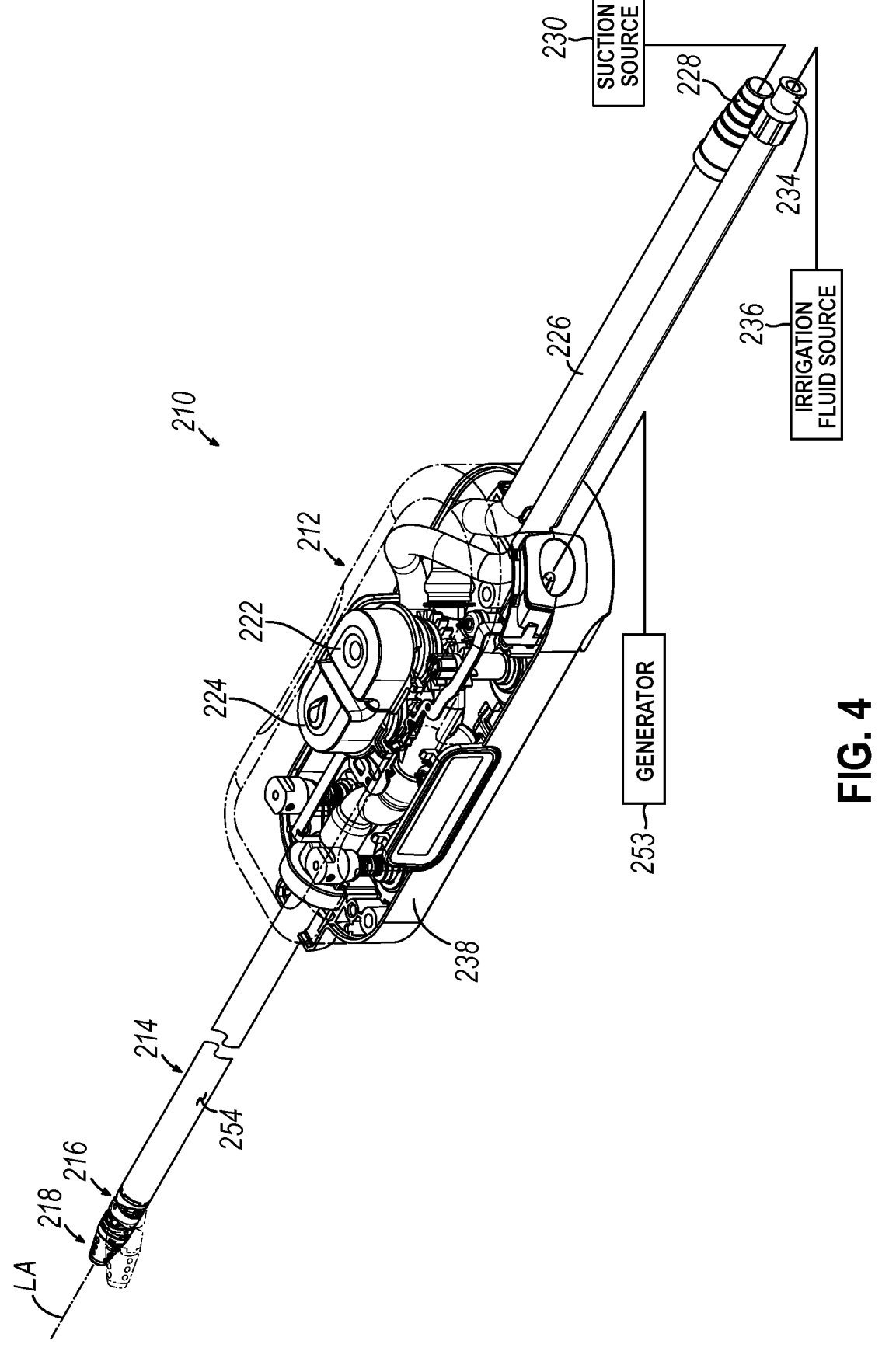
FIG. 4 depicts a perspective view of a second example of a surgical instrument, configured with use with the table-based robotic system of FIG. 1 as well as the robotic arm and the tool drive of FIG. 2.

FIG. 4 shows a second example of a surgical instrument (210) configured with use with robotic surgical system (10) including robotic arms (16, 110) and tool drivers (22, 112) of FIGS. 1-2. Surgical instrument (210) may be used in place of surgical instrument (24, 114). As previously described, tool driver (112) includes stage (126) and carriage (128), with carriage (128) being configured to move relative to stage (126) to move surgical instrument (210) relative to patient (P). Surgical instrument (210) includes a body (shown as a tool drive adapter (212)), a shaft assembly (214), an articulatable section (216), and an end effector (218).

A distal end (220) of surgical instrument (210) is configured to be inserted into patient (P). In some versions, distal end (220) may be inserted into patient (P) through a trocar (not shown). As shown, tool drive adapter (212) extends distally from robotic arm (16, 110). Similar to tool drive adapter (124), tool drive adapter (212) is configured to couple with tool driver (112), so that surgical instrument (210) is operatively coupled with robotic arm (16, 110). Tool drive adapter (212) is configured to move along stage (126). With continued reference to FIG. 4, tool drive adapter (212) includes a suction button (222) and an irrigation fluid button (224). A first end of a suction tubing (226) is coupled with suction button (222) and a second end is coupled with a suction fitting (228). Suction fitting (228) may be coupled with a vacuum source (230). Irrigation fluid tubing (232) extends proximally from suction button (222). A first end of an irrigation fluid tubing (232) is coupled with irrigation fluid button (224) and a second end is coupled with an irrigation fluid fitting (234). Irrigation fluid fitting (234) may be coupled with an irrigation fluid source (236) (e.g., saline).

Figure 5:
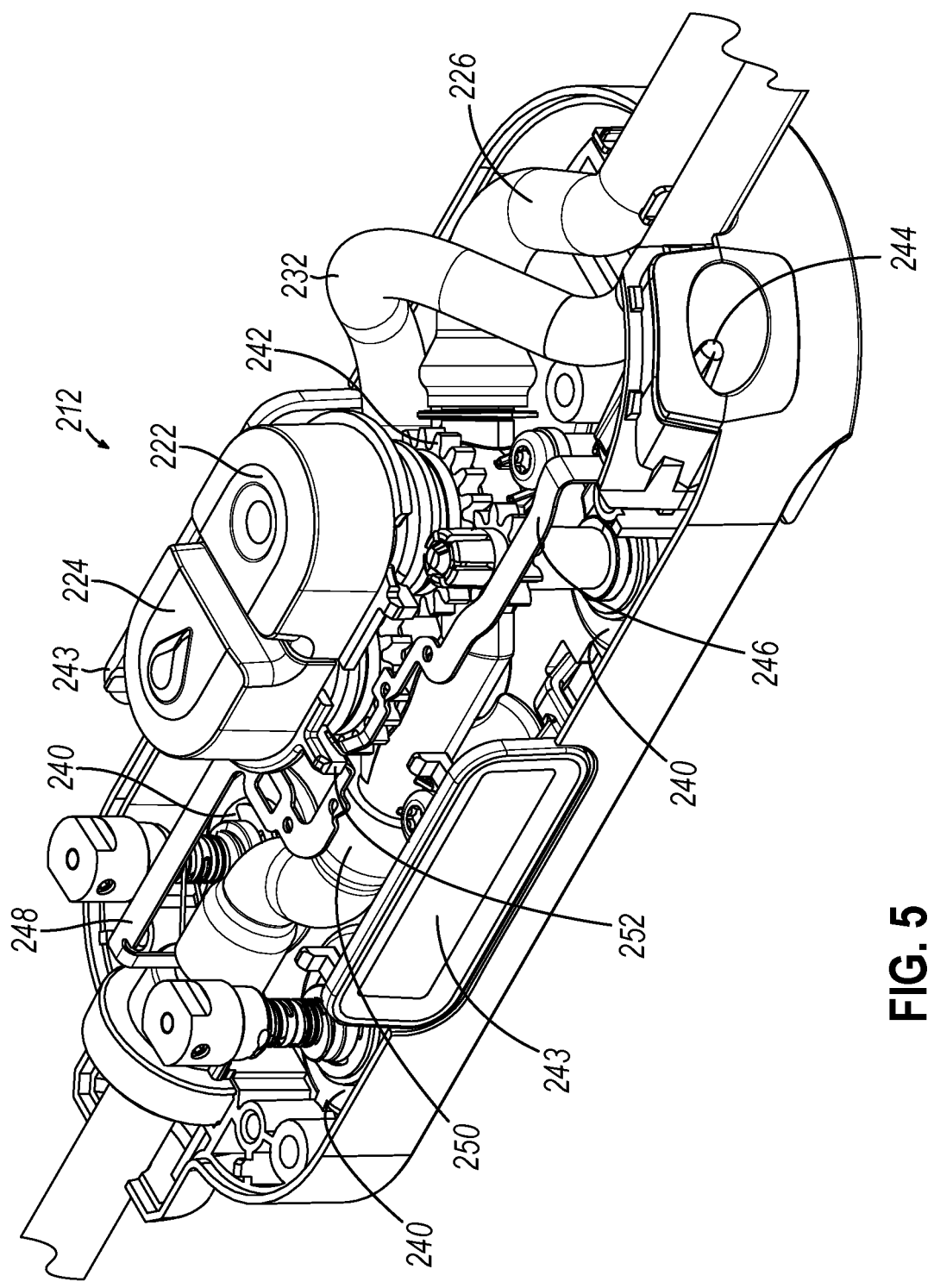
FIG. 5 depicts an enlarged perspective view of a body of the surgical instrument of FIG. 4 with the housing removed to reveal internal components including an example of an energy breaker.

FIG. 5 shows tool drive adapter (212) of FIG. 4 with a housing (238) of tool drive adapter (212) removed to reveal internal components. Tool drive adapter (212) includes a plurality of rotary drives (240) similar to rotary drives (136a-f), a drive train assembly (242), decoupling features (243), a power connection (244), first and second metallic brackets (246, 248), and a common fluid tube (250). While a common fluid tube (250) is shown, separate tubes may be used for suction and irrigation fluid. A generator (253) may be coupled with power connection (244) to provide electrosurgical energy to surgical instrument (210).

The application irrigation fluid may be initiated through actuation of irrigation fluid button (224). It may be desirable to avoid providing irrigation fluid to distal end (220) at the same time electrosurgical energy is being applied to avoid electrically conducting the irrigation fluid (e.g., the saline). In some instances, energizing irrigation fluid (e.g., saline) may cause the tissue to seize. As shown in FIG. 5, tool drive adapter (212) includes an example of an energy breaker (251). Energy breaker (251) may be activated manually by a user or automatically by robotic surgical system (10). Energy breaker (251) may prevent energizing irrigation fluid by breaking the flow of current in response to irrigation fluid (e.g., saline) being applied by manual actuation or robotic actuation. Energy breaker (251) may break the flow of current in response to irrigation fluid button (224) being depressed, either through manually pressing irrigation fluid button (224) or through irrigation fluid button (224) being depressed during robotic actuation. Energy breaker (251) may prevent energizing the irrigation fluid by terminating the flow of current to electrode in response to the application of irrigation fluid.

Figure 6A:
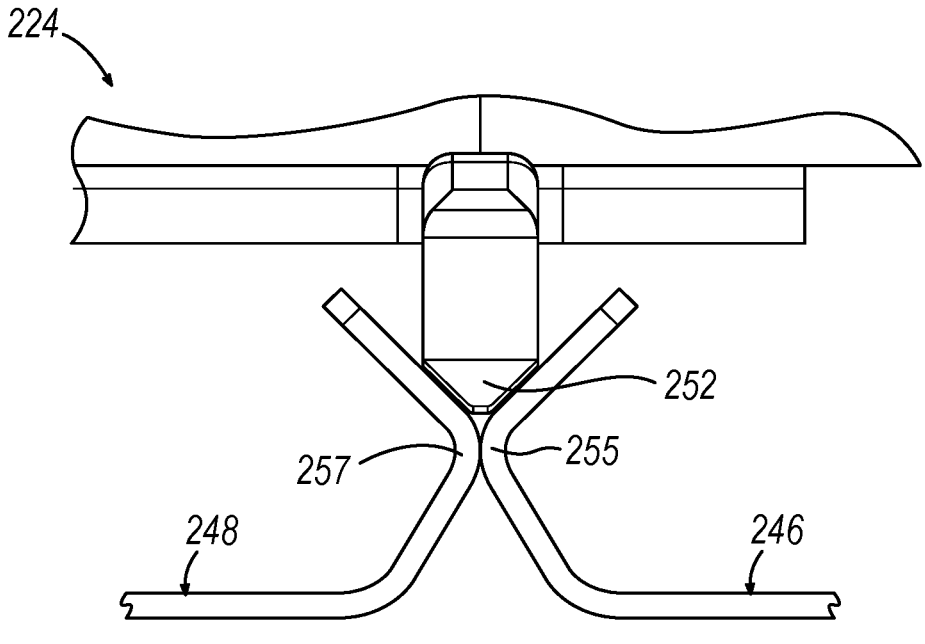
FIG. 6A depicts a schematic side elevational view of the energy breaker of FIG. 5 in a connected configuration.
Figure 6B:
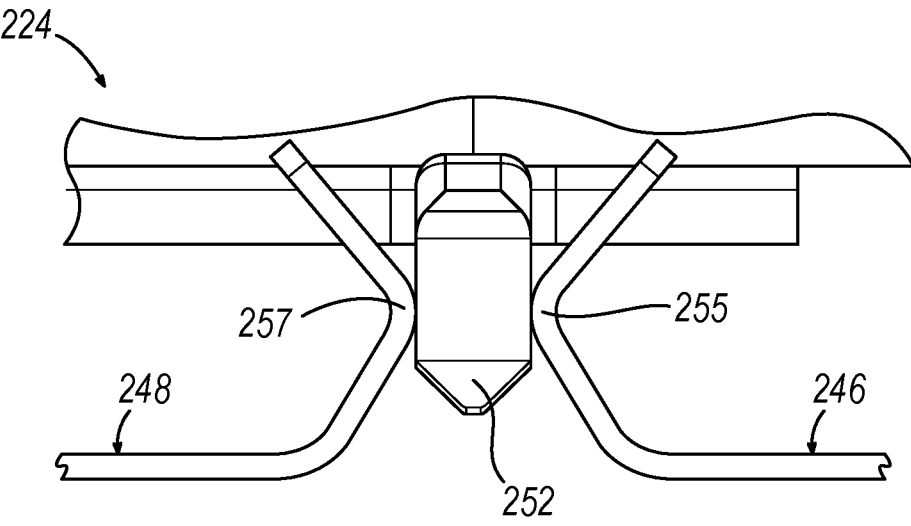
FIG. 6B depicts a schematic side elevational view of the energy breaker similar to FIG. 6A, but moved to a disconnected configuration.

Energy breaker (251) is shown in the form of a projection (252) of irrigation fluid button (224). FIG. 6A shows energy breaker (251) in a connected configuration, and FIG. 6B shows energy breaker (251) moved to a disconnected configuration. In the connected configuration of FIG. 6A, projection (252) may be spaced a distance from or in abutting contact with ends (255, 257) of first and second metallic brackets (246, 248), while still allowing ends (255, 257) to contact one another. In other words, projection (252) allows for first and second metallic brackets (246, 248) to contact each other when irrigation fluid button (224) is not depressed. Conversely, in the disconnected configuration of FIG. 6B, projection (252) separates and extends between ends (255, 257) of first and second metallic brackets (246, 248) preventing the current from passing from end (255) to end (257). End (255) is not in contact with end (257) in the disconnected configuration. Particularly, projection (252) separates end (255) of first metallic bracket (246) from end (257) of second metallic bracket (248) when irrigation fluid button (224) is depressed. Projection (252) may function as a simple line break to break the flow of electricity. Energy breaker (251) prevents current from traveling proximally (e.g., to robot arm (16, 110) or irrigation fluid source (236). Energy breaker (251) prevents current from traveling distally to shaft assembly (214), articulatable section (216), end effector (218), or to patient (P).

Figure 7:
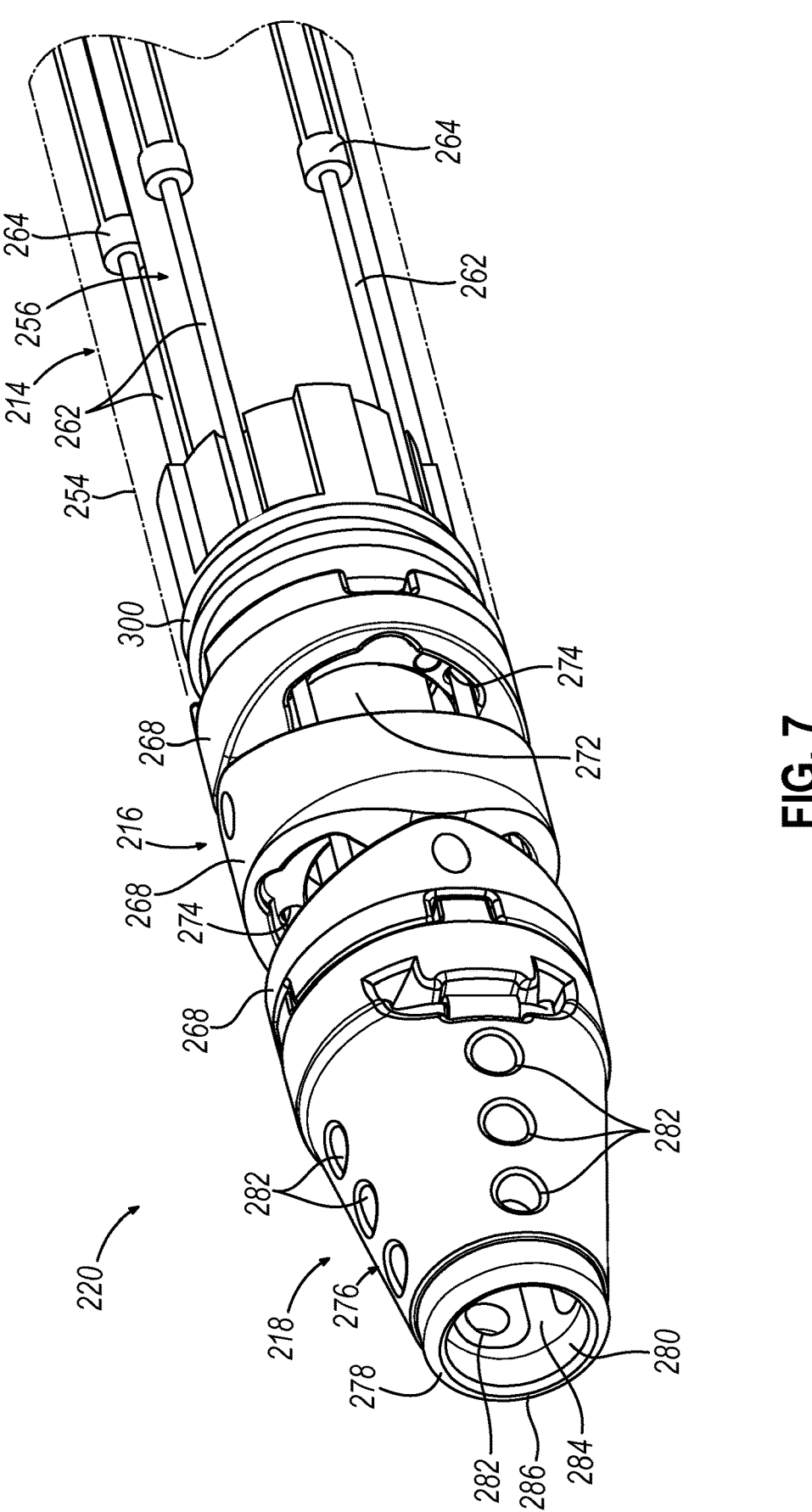
FIG. 7 depicts an enlarged perspective view of a distal end of the surgical instrument of FIG. 4 in a straight configuration, the distal end including a portion of a shaft assembly, an articulatable section, and an end effector, with an outer shaft of the shaft assembly being shown in broken lines.
Figure 8:
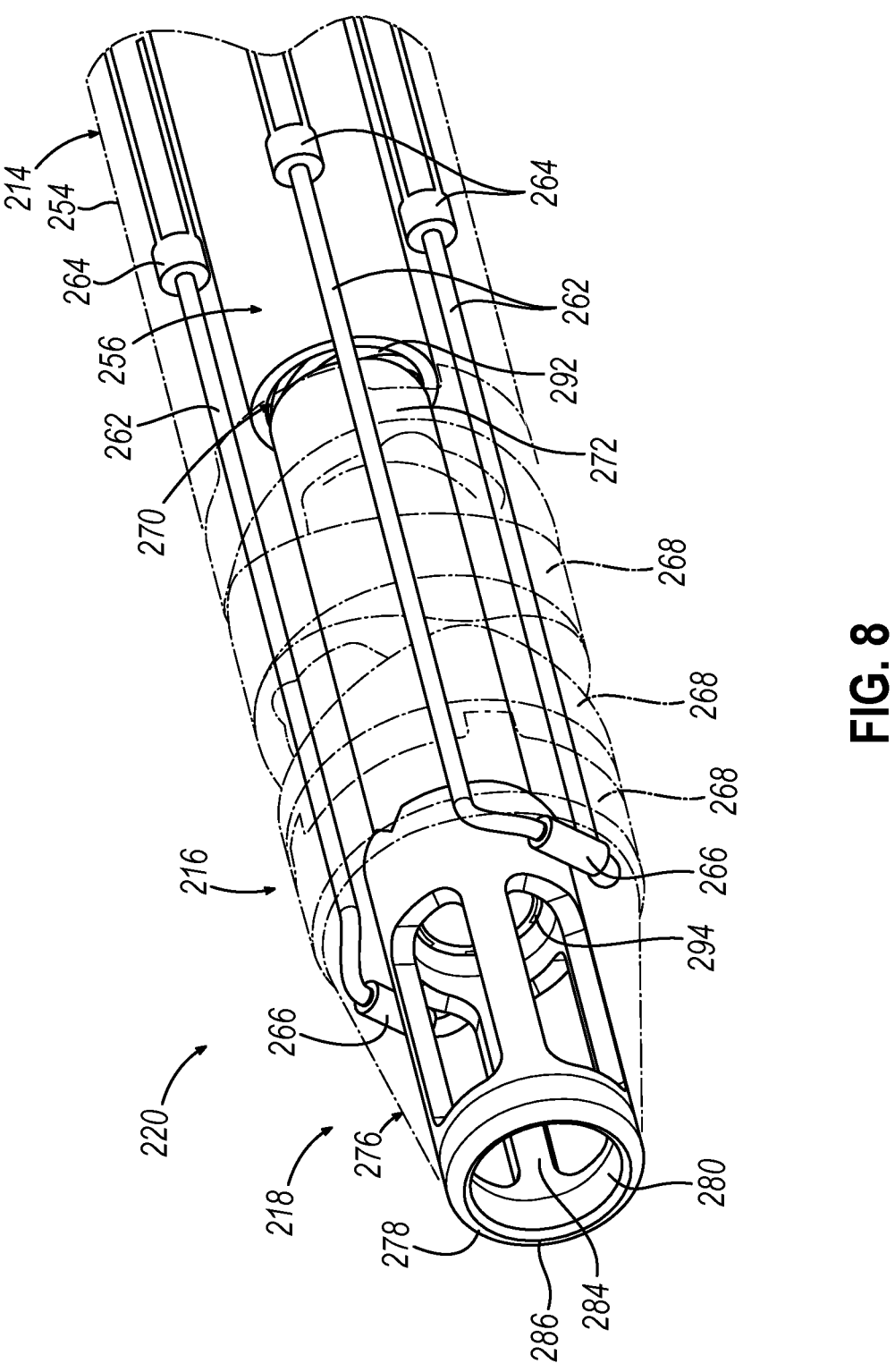
FIG. 8 depicts a perspective view of the distal end of the surgical instrument of FIG. 7, with a nozzle of the end effector and articulatable segments of the articulatable section shown in broken lines.
Figure 9:
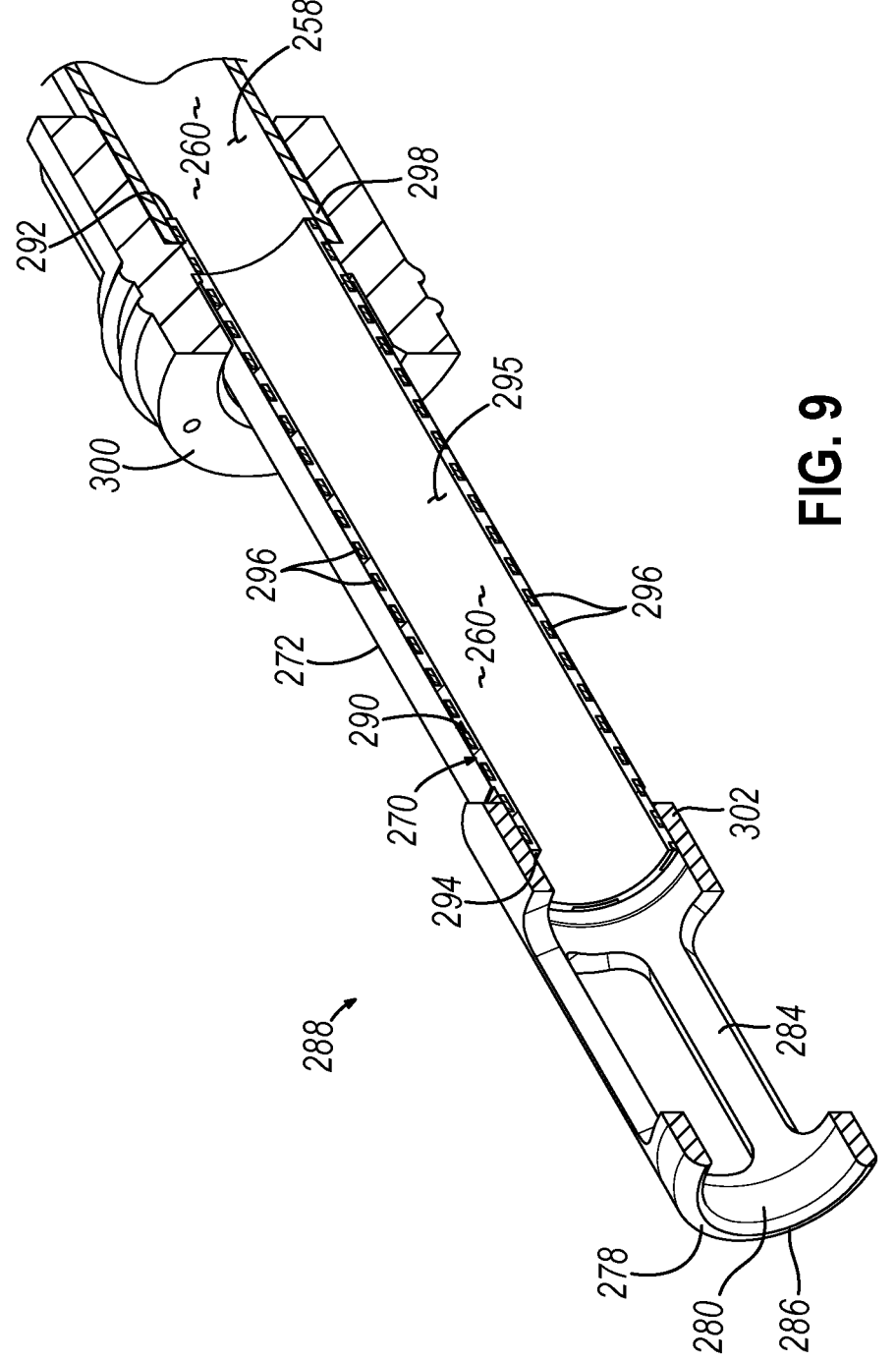
FIG. 9 depicts a sectional perspective view of an energy transfer system of the distal end of the surgical instrument of FIG. 8.

FIGS. 7-8 show distal end (220) of surgical instrument (210) in a straight configuration. As shown, distal end (220) includes a portion of shaft assembly (214), articulatable section (216), and end effector (218). Shaft assembly (214) extends distally from tool drive adapter (212) along a longitudinal axis (LA). Shaft assembly (214) includes an outer shaft (254) and an inner metallic conduit (256). FIG. 7 shows outer shaft (254) in broken lines. Inner metallic conduit (256) allows for current to travel from tool drive adapter (212) to articulatable section (216). As shown in FIG. 9, inner metallic conduit (256) extends through shaft assembly (214) and includes an inner surface (258) that defines a fluid passageway (260) to transport irrigation fluid and debris therethrough. As used herein, debris is intended to include portions of tissue, bodily fluids, foreign substances, and/or smoke. For example, fluid passageway (260) may simultaneously remove tissue and/or smoke from patient (P) to improve visibility to the user (e.g., when utilizing an endoscope). Shaft assembly (214) includes at least one cable (262). While three cables (262) are shown, more or fewer cables (262) are also envisioned. Relative moment of cables (262) along longitudinal axis (LA) causes articulatable section (216) to move between the straight configuration (see FIG. 7) and the articulated configuration (see FIG. 11). As shown, cables (262) include connectors (264) and a distal U-shaped portion (266) that extends away from longitudinal axis (LA).

Articulatable section (216) is disposed between shaft assembly (214) and end effector (218). Articulatable section (216) is configured to deflect end effector (218) between the straight configuration (see FIG. 7) where end effector (218) extends along longitudinal axis (LA) and an articulated configuration (see FIG. 11) where end effector (218) is deflected away from longitudinal axis (LA). As shown, articulatable section (216) includes a plurality of articulatable segments (268), at least one flexible metallic feature (270), and a flexible tube (272). As shown, cables (262) extend through apertures (274) of articulatable segments (268). As will be described in greater detail below with reference to FIGS. 9-10, flexible metallic feature (270) is configured to transmit electrosurgical energy through articulatable section (216) in a fully straight configuration, a fully articulated configuration, and configurations therebetween. Flexible metallic feature (270) includes at least one of stainless steel, copper, or silver. Inner metallic conduit (256) and flexible metallic feature (270) each surround different longitudinal portions of fluid passageway (260). Flexible metallic feature (270) is in electrical communication with inner metallic conduit (256). Flexible metallic feature (270) passes current through to articulatable section (216) to energize electrode (278) positioned within end effector (218) without utilizing a separate lumen (not shown) or decreasing the available cross-sectional area within fluid passageway (260). Flexible metallic feature (270) maximizes suction and/or irrigation fluid flow through fluid passageway (260) without additional wiring extending within fluid passageway (260).

End effector (218) includes a nozzle (276) and an electrode (278). FIG. 8 shows nozzle (276) of end effector (218) in broken lines. End effector (218) may be radially symmetric and have a radius of a ring. However, end effector (218) may have a variety of suitable shapes and sizes. Nozzle (276) includes at least one aperture in fluid communication with fluid passageway (260). As shown, nozzle (276) includes a distal aperture (280) and a plurality of laterally extending apertures (282). Apertures (280, 282) are configured to receive an irrigation fluid therethrough for irrigating the tissue and/or a receive a vacuum therethrough for removing debris from patient (P). For example, apertures (280, 282) are configured to at least one of provide irrigation fluid to the tissue, remove tissue from patient (P), or remove smoke from patient (P). Apertures (280, 282) are disposed between electrode (278) and articulatable section (216). Apertures (280, 282) are in fluid communication with inner metallic conduit (256). Distal aperture (280) extends concentrically through electrode (278).

Electrode (278) is configured to apply electrosurgical energy to tissue to denature and/or coagulate the tissue. Electrode (278) is configured to provide micro-morcellation using energy to denature and electrocauterize the tissue being dissected. Unlike an augur or morcellator where the cutting action is mechanical, the cutting action of electrode (278) is electrical. For example, electrode (278) may remove a hard tumor by systematically skiving off successive portions of the hard tumor until removed. Electrode (278) is positioned at a distal most tip (286) of end effector (218). Distal most tip (286) may be flat, rounded, or chamfered. The shape of distal most tip (286) may influence the suction force through distal aperture (280). An intermediate metallic feature (284) is disposed between and electrically coupled with electrode (278) and flexible metallic feature (270) to transfer energy from articulatable section (216) to electrode (278). As shown, electrode (278) includes a continuous metallic ring (monopolar ring) that is configured to apply monopolar energy to the tissue. In some versions, end effector (218) includes a second electrode (see FIG. 14) configured to coordinate with electrode (278) to apply bipolar energy to the tissue. For example, the continuous metal ring may be integrally formed together as a unitary piece for monopolar energy application or segmented for bipolar energy application. The application of monopolar energy may cause more smoke than the application of bipolar energy. As a result, it is beneficial to remove this smoke to improve visibility.

Figure 10:
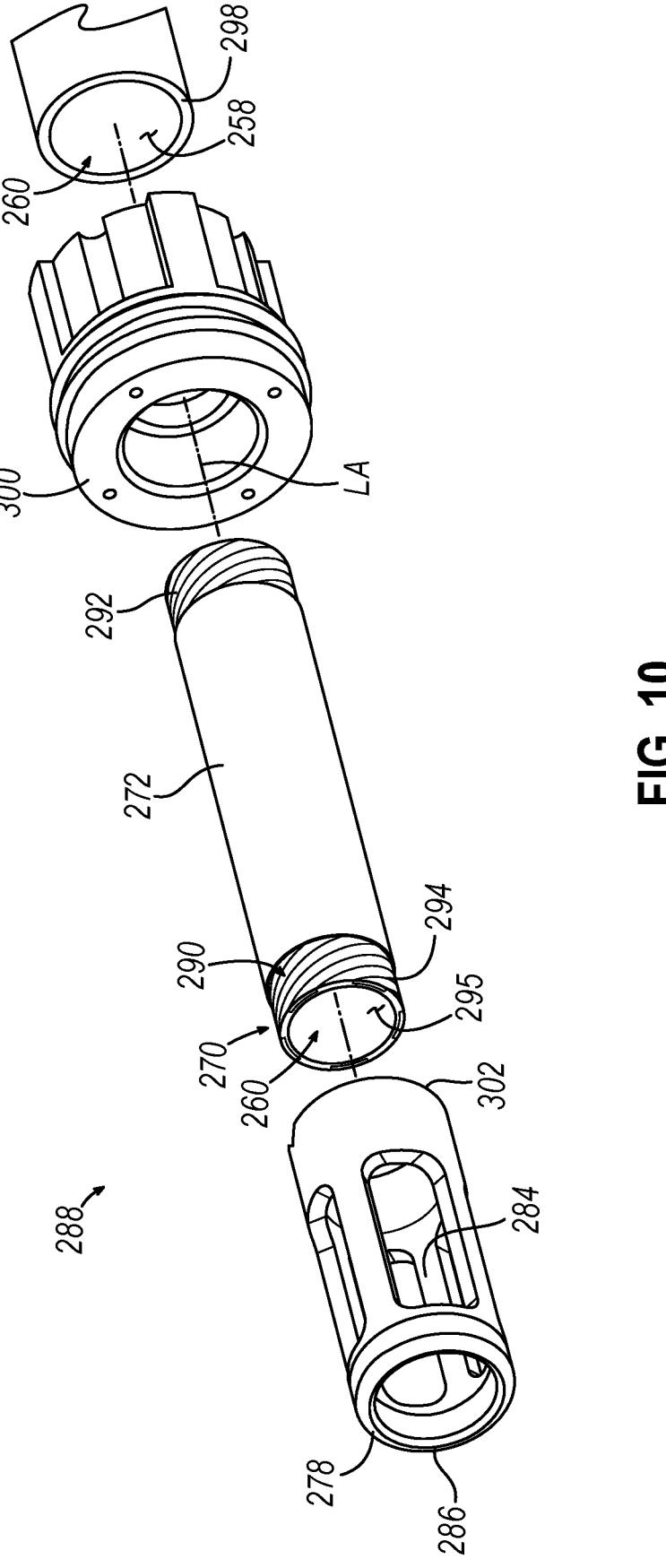
FIG. 10 depicts an exploded perspective view of the energy transfer system of the distal end of the surgical instrument of FIG. 9.

FIGS. 9 and 10 show energy transfer system (288) of distal end (220) of surgical instrument (210). Particularly, FIG. 9 shows a sectional view of energy transfer system (288) of FIG. 8, and FIG. 10 shows an exploded view of energy transfer system (288). Energy transfer system (288) makes use of flexible metallic feature (270) to carry the current rather than incorporating additional wiring through articulatable section (216). As shown in FIGS. 8-10, flexible metallic feature (270) includes a flexible metallic helical member (290) configured to both transmit current to electrode (278) and provide strength to articulatable section (216). Flexible metallic helical member (290) includes a proximal end (292), a distal end (294), and a helical coil (296) extending therebetween. Flexible metallic helical member (290) is at least partially embedded within flexible tube (272). As shown, helical coil (296) fully embedded within flexible tube (272) with proximal and distal ends (292, 294) being exposed to allow for electrical continuity. Flexible tube (272) defines inner surface (295) that defines fluid passageway (260). In some versions, flexible metallic helical member (290) is completely embedded or encapsulated within flexible tube (272) except for energy transferring portions (e.g., proximal and distal ends (292, 294)) that are connected with shaft assembly (214) and end effector (218).

Regarding energy transfer system (288), current may be provided by a generator (253) that is removably coupled with power connection (244). Current may then be transferred from power connection (244) to first metallic bracket (246) which may be in electrical contact with second metallic bracket (248) when not separated by projection (252) of irrigation fluid button (224). Second metallic bracket may be electrically coupled with inner metallic conduit (256) that extends through shaft assembly (214). As shown in FIG. 9, a distal end (298) of inner metallic conduit (256) is coupled with proximal end (292) of flexible metallic helical member (290). A sleeve (300) may electrically insulate proximal end (292) of flexible metallic helical member (290). Current travels helically through respective helical coils (296) until reaching distal end (294) of flexible metallic helical member (290). Distal end (298) is coupled with a proximal end (302) of intermediate metallic feature (284). Intermediate metallic feature (284) may be coupled with electrode (278) so that so that electrode (278) may apply electrosurgical energy to tissue.

Given the tight spaces, it may be challenging to route power to electrode (278) through a flexible portion of surgical instrument (210) that is configured to be articulated.

Figure 11:
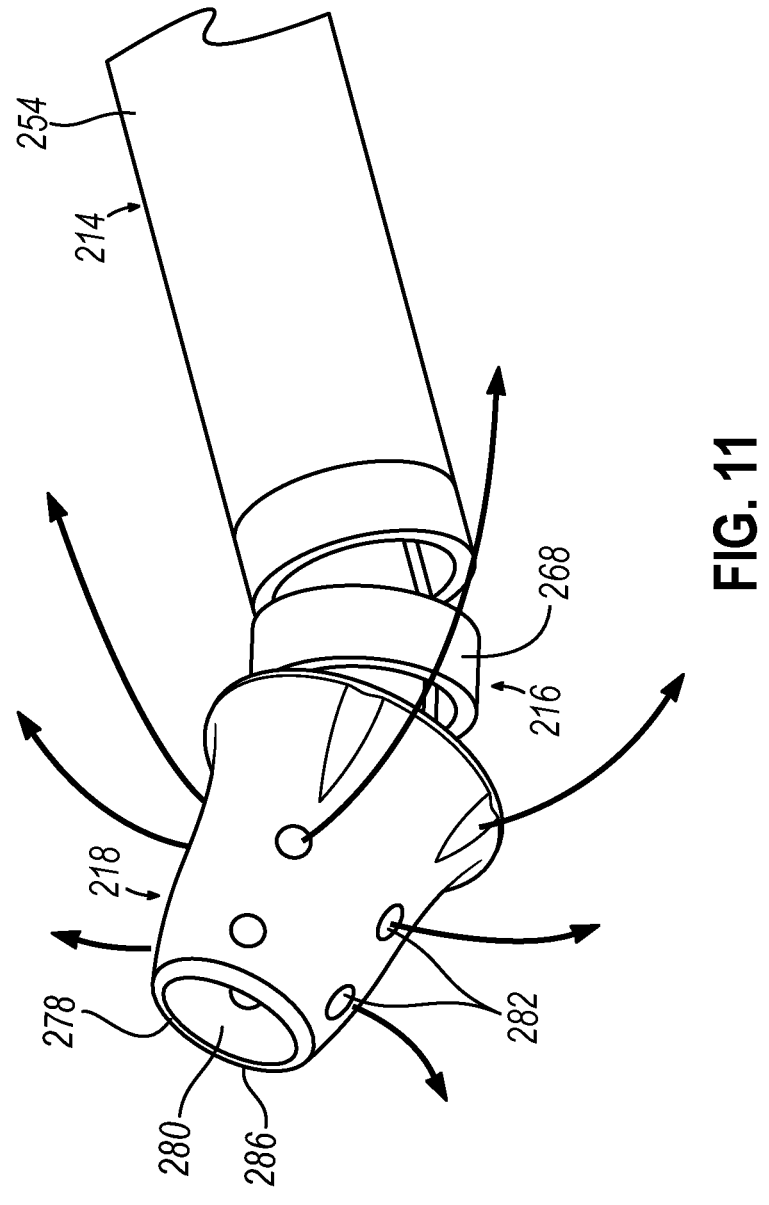
FIG. 11 depicts a perspective view of a distal end of the surgical instrument of FIG. 7 in an articulated configuration with irrigation fluid exiting from a plurality of lateral apertures of the end effector.

Without flexible metallic feature (270) (e.g., flexible metallic helical member (290) or an additional connection element), electrode (278) cannot be suitably energized. Flexible metallic feature (270) performs multiple functions. Reinforcing flexible tube (272) with flexible metallic feature (270) may strengthen fluid passageway (260) through articulatable section (216) when applying suction to evacuate tissue and smoke from patient (P). Additionally, reinforcing flexible tube (272) with flexible metallic feature (270) allows for articulation of articulatable section (216) without occupying additional space within fluid passageway (260) or another lumen. To maximize component functionality, inner metallic conduit (256) may be used to pass electrosurgical energy from tool drive adapter (212) to electrode (278) (e.g., which may be in the form of an energized monopolar ring disposed at distal most tip (286)). FIG. 11 shows a perspective view of a distal end (220) of surgical instrument (210) of FIG. 7 in an articulated configuration with irrigation fluid exiting from laterally extending apertures (282) of nozzle (276).

Surgical instrument (210) allows for micro-morcellation, cauterization, ablation, and other tissue effecting energy usage using energy to denature, coagulate and/or effect the tissue being dissected, as well as simultaneous smoke/tissue evacuation during dissection, lavage, and articulation. This simultaneous smoke/tissue evacuation could be either directly controlled by the surgeon or triggered automatically by the control system when energy is applied, without further input by the user. Surgical instrument (210) may be used as a retractor and for non-energized blunt tissue dissection or energized dissection (monopolar or bipolar). Additionally, surgical instrument (210) allows the user to lavage and apply suction for smoke/tissue evacuation. For example, surgical instrument (210) may simultaneously provide suction and electrosurgical energy, and switch to provide irrigation fluid without electrosurgical energy.

A surgeon may control surgical instrument (210) at a console, while an assistant may reside at another location (near patient (P)). Robotic surgical system (10) may utilize mode switching for instances where the functionality of surgical instrument (210) is limited by the number of available controls. For mode switching, a user is able to increase the number of controls by switching to a second or third functionalities for the same control (e.g., button, joystick, foot pedal etc.). For example, a user may pinch their fingers to switch from a first mode to a second mode. A first mode may provide suction and irrigation through usage of the foot pedals. A second mode be initiated through double tapping the pinch of the hand control to switch modes and thus allow the surgeon to apply electrosurgical energy and suction through usage of the foot pedals. A third mode may be initiated to apply electrosurgical energy and irrigation through usage of the foot pedals. In some versions, a user may activate multiple controls (e.g., buttons, joysticks, pedals) at the same time to apply irrigation fluid and suction at the same time and remove power to electrode (278). In some versions, robotic surgical system (10) may automatically activate smoke evacuation.

C. Second Example of a Distal End of a Surgical Instrument

Figure 12:
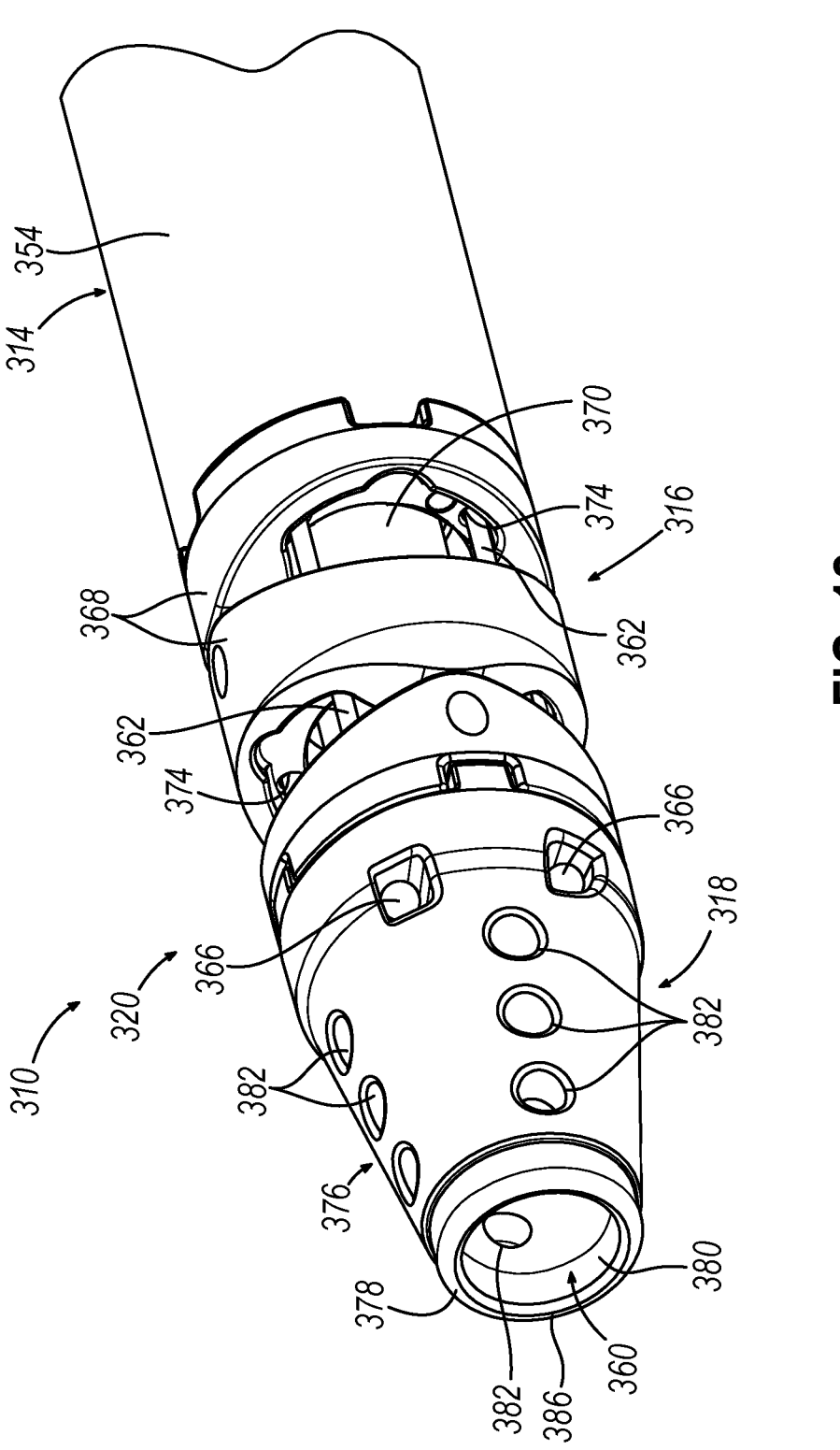
FIG. 12 depicts a perspective view a second example of a distal end of a surgical instrument in a straight configuration, the distal end including a portion of a shaft assembly, an articulatable section, and an end effector.
Figure 13:
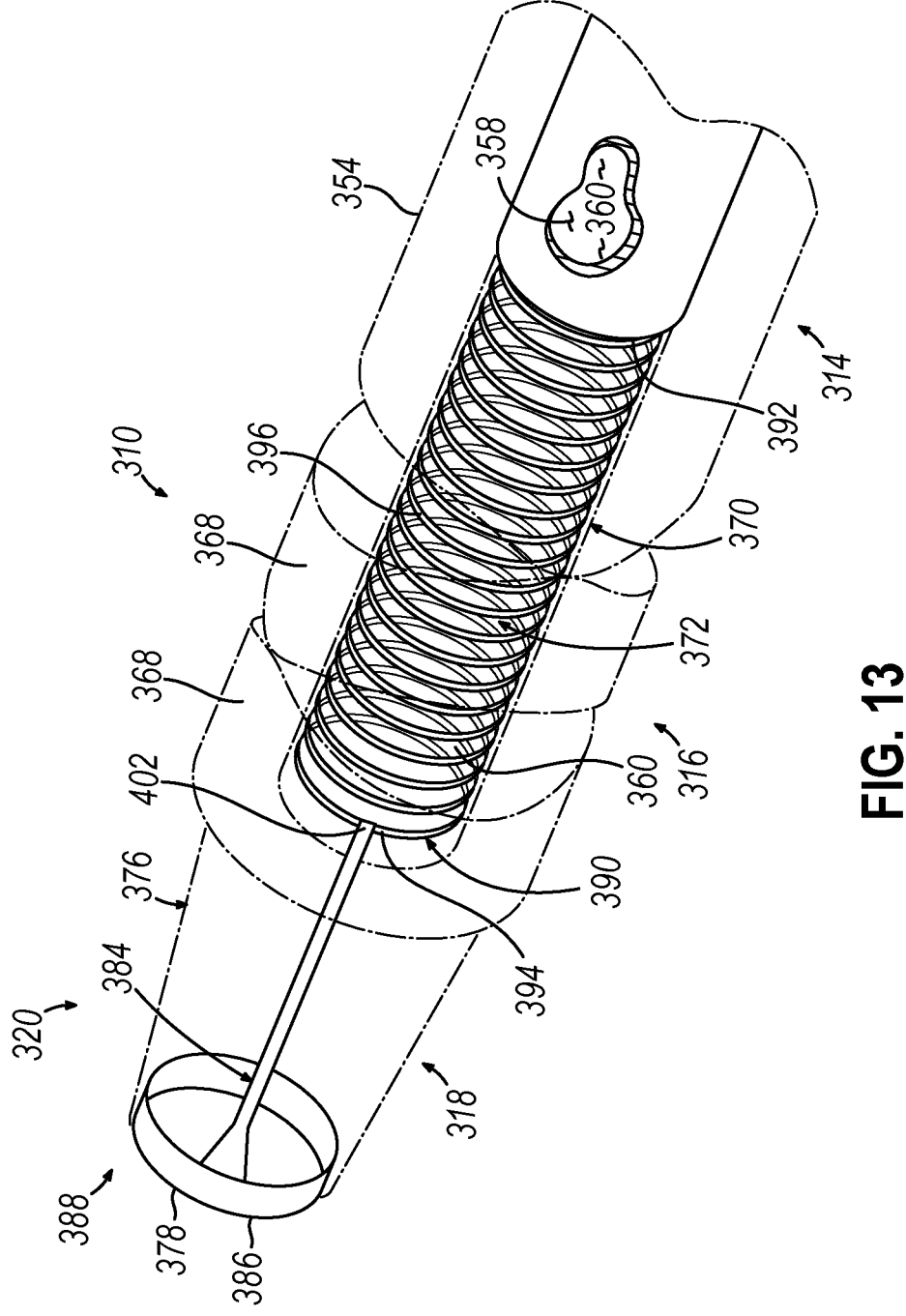
FIG. 13 depicts a perspective view of the distal end of FIG. 12, with a nozzle of the end effector and articulatable segments of the articulatable section shown in broken lines.

FIGS. 12-13 show a second example of a distal end (320) of a surgical instrument (310) in a straight configuration. Surgical instrument (310) is similar to surgical instrument (210) except as where otherwise indicated below. Similar to distal end (220), distal end (320) includes a portion of a shaft assembly (314), an articulatable section (316), and an end effector (318).

Shaft assembly (314) extends distally from a tool drive adapter (not shown) but similar to tool drive adapter (212) along a longitudinal axis (LA). Shaft assembly (314) includes an outer shaft (354) and an inner metallic conduit (356). As shown in FIG. 13, inner metallic conduit (356) extends through shaft assembly (314) and includes an inner surface (358) that defines a fluid passageway (360) to transport fluids (incompressible liquids and/or compressible gases) therethrough. Articulatable section (316) includes a plurality of articulatable segments (368), at least one flexible metallic feature (370), and a flexible tube (372). As shown in FIG. 12, a plurality of longitudinally extending cables (362) control rotation of end effector (318). For example, four cables (362) with distal spherical tips (366) may articulate end effector (318). As shown, cables (362) extend through apertures (374) of articulatable segments (368).

End effector (318) includes a nozzle (376), an electrode (378), and a ribbon feature (384). Nozzle (376) includes at least one aperture in fluid communication with fluid passageway (360). As shown, nozzle (376) includes a distal aperture (380) and a plurality of laterally extending apertures (382). Whereas end effector (218) includes intermediate metallic member (284), end effector (318) includes ribbon feature (384) that electrically couples flexible metallic helical member (390) with electrode (378). As shown, electrode (378) includes a continuous metallic ring (monopolar ring) that is configured to apply monopolar energy to the tissue. In some versions, end effector (318) includes a second electrode (see FIG. 14) configured to coordinate with electrode (378) to apply bipolar energy to the tissue. Electrode (378) is positioned at a distal most tip (386) of end effector (318).

FIG. 13 shows distal end (320) of FIG. 12, with nozzle (376) of end effector (318) and articulatable segments (368) of articulatable section (316) shown in broken lines. Current travels helically through respective helical coils (396) until reaching distal end (398) of flexible metallic helical member (390). Distal end (398) is coupled with a proximal end (402) of ribbon feature (384). Ribbon feature (384) may be coupled with electrode (378) to apply electrosurgical energy to tissue.

Regarding energy transfer system (388), current may be provided to inner metallic conduit (356) that extends through shaft assembly (314) in a manner similar to surgical instrument (210). As shown in FIG. 13, a distal end (398) of inner metallic conduit (356) is coupled with proximal end (392) of flexible metallic helical member (390). Current travels helically through respective helical coils (396) until reaching distal end (394) of flexible metallic helical member (290). Distal end (398) is coupled with a proximal end (402) of ribbon feature (384). Ribbon feature (384) may be coupled with electrode (378) so that electrode (378) may apply electrosurgical energy to tissue.

D. Third Example of a Distal End of a Surgical Instrument

Figure 14:
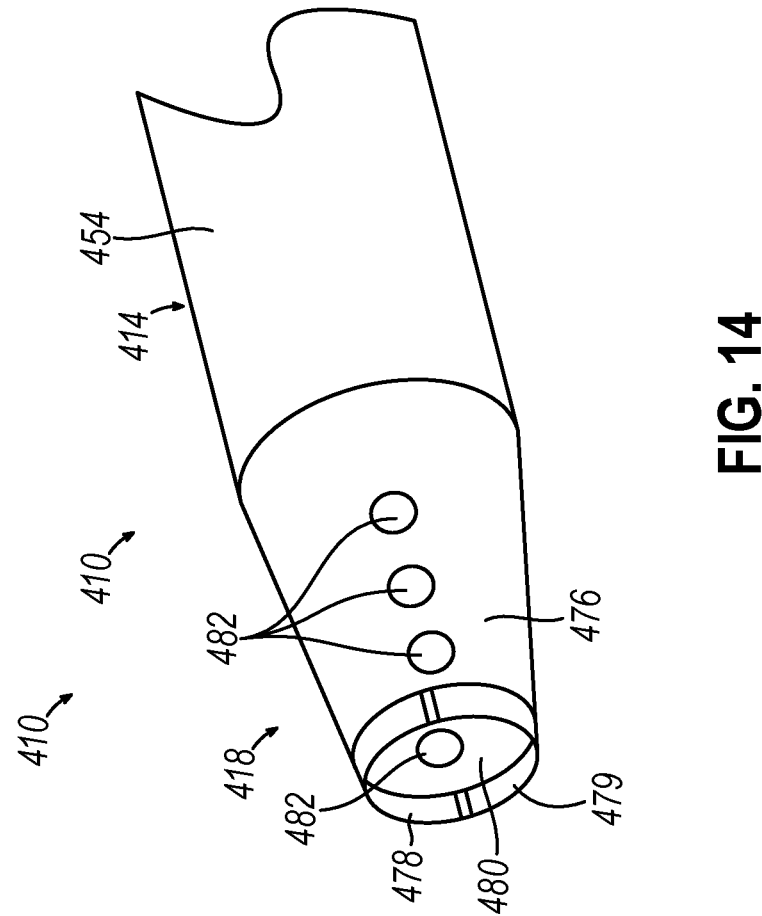
FIG. 14 depicts a schematic perspective view a third example of a distal end of a surgical instrument.

FIG. 14 shows a schematic perspective view third example a distal end (420) of a surgical instrument (410) in a straight configuration. Surgical instrument (410) is similar to surgical instrument (210) except as where otherwise indicated below. As shown in FIG. 14, surgical instrument (410) does not articulate relative to the longitudinal axis (LA). Whereas surgical instrument (210) includes articulatable section (216) to move between the straight configuration (see FIG. 7) and the articulated configuration (see FIG. 11), distal end (420) is not shown as including an articulatable section. Instead, shaft assembly (414), is coupled with end effector (418).

Similar to shaft assembly (214), shaft assembly (414) includes an outer shaft (454) and an inner metallic conduit (not shown). The inner metallic conduit may be directly coupled with electrode (478) or include an intermediate metallic feature (not shown) but similar to intermediate metallic feature (284). End effector (418) includes a nozzle (476), a first electrode (478), and a second electrode (479). As shown, nozzle (476) includes a distal aperture (480) and a plurality of laterally extending apertures (482). In some versions, surgical instrument (410) may incorporate an energized ring tip. Instead of first and second electrodes (478, 479) being configured to provide bipolar energy, an electrode being configured to provide monopolar energy. Alternatively, end effector (418) may be similar to end effectors (218, 318).

E. Example of an Energy Breaker

It may be desirable to avoid providing irrigation fluid to distal end (220, 320, 420) at the same time electrosurgical energy is being applied to avoid electrically conducting the irrigation fluid (e.g., the saline). In some instances, energizing irrigation fluid (e.g., saline) may cause the tissue to seize.

Figure 15:
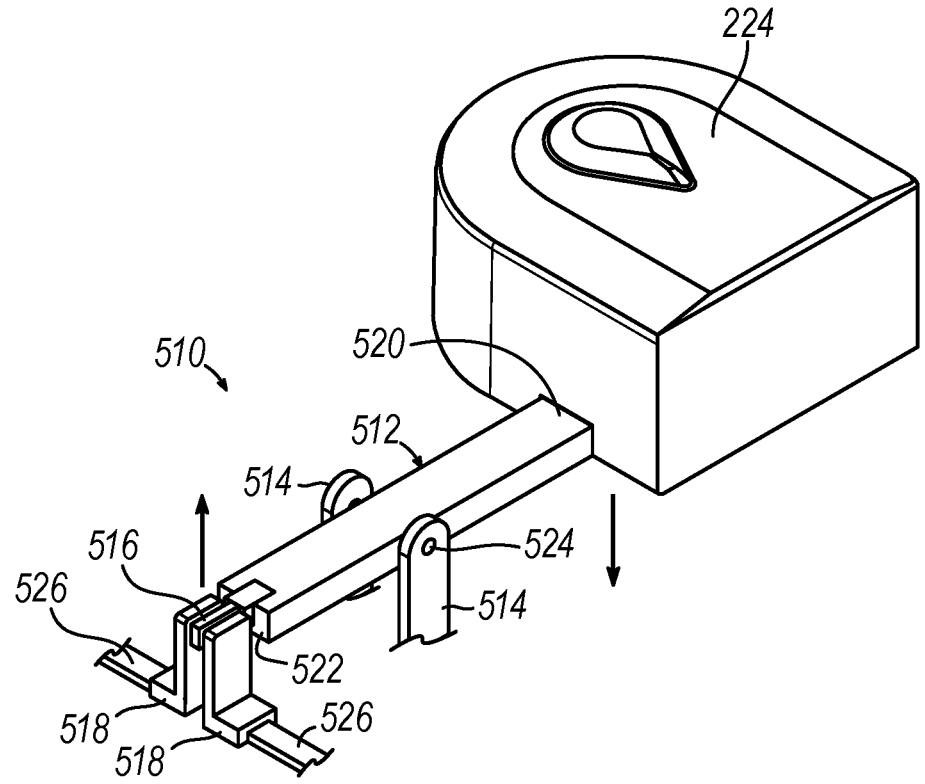
FIG. 15 depicts a schematic perspective view of another energy breaker for use with the body of FIG. 4.

FIG. 15 shows a schematic view of an exemplary energy breaker (510) for use with tool drive adapter (212) of FIG. 3. Energy breaker (510) may be configured for use with surgical instruments (210, 310, 410) described above with reference to FIGS. 4-14. For example, energy breaker (510) may be used in place of energy breaker (251) described above with reference to FIGS. 5-6B. Energy breaker (510) is configured to prevent energizing irrigation fluid by terminating the flow of current to electrode (278, 378, 478) in response to the application of irrigation fluid being initiated. For example, the application irrigation fluid may be initiated using irrigation fluid button (224). While energy breaker (510) is shown as being positioned in tool drive adapter (212), it is also envisioned that energy breaker (510) may be positioned along other portions of surgical instrument (210, 310, 410). Energy breaker (510) may be activated manually by a user or automatically by robotic surgical system (10). Energy breaker (510) may include a variety of mechanisms including at least one switch. A switch may function as a simple line break to break the flow of electricity. For example, exemplary switches may include at least one of a relay switch, a gate switch, a dome switch, a push button switch, or a toggle switch.

Figure 16A:
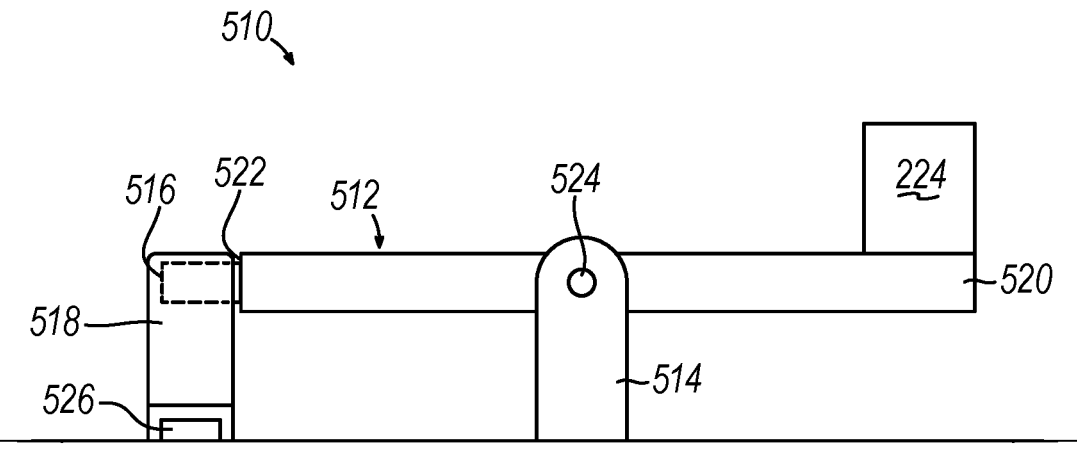
FIG. 16A depicts a schematic perspective view of the energy breaker of FIG. 15 in a connected configuration.
Figure 16B:
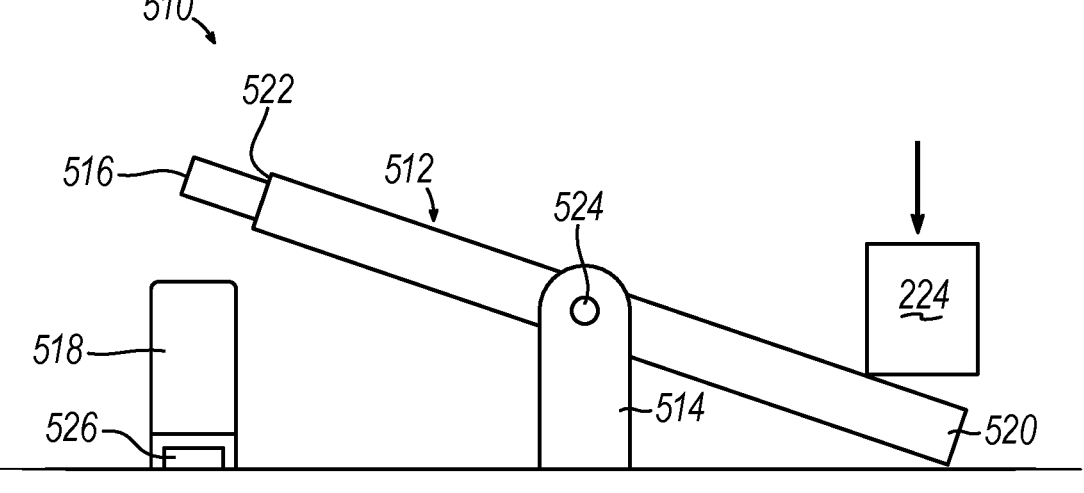
FIG. 16B depicts a schematic perspective view of the energy breaker similar to FIG. 16A, but moved to a disconnected configuration.

FIG. 16A shows energy breaker (510) in a connected configuration, and FIG. 16B shows energy breaker (510) moved to a disconnected configuration. As shown, energy breaker (510) includes an activation member (512), at least one support (514), an object (516) (which may also be referred to as a flag), and one or more receivers (518). Activation member (512) includes opposing first and second ends (520, 522). Activation member (512) is configured to pivot about a pivot point (524) between the connected configuration (see FIG. 16A), and the disconnected configuration (see FIG. 16B). In the connected configuration of FIG. 16A, object (516) is sensed by, and positioned at least partially between receivers (518). In the connected configuration, the switch is closed. For example, one or more wires (526) may communicate to the control system that the switch is closed allowing for the application of the electrosurgical energy to the tissue. In the disconnected configuration of FIG. 16B, object (516) is spaced a distance from receiver (518), and as a result, not sensed by receiver (518). For example, in the disconnected configuration, one or more wires (526) may communicate to the control system that the switch is open preventing the application of the electrosurgical energy to the tissue.

Energy breaker (510) may prevent energizing irrigation fluid by breaking the flow of current in response to irrigation fluid (e.g., saline) is being applied by robotic actuation or manual actuation. Energy breaker (510) may break the flow of current in response to irrigation fluid button (224) is depressed either through manually pressing irrigation fluid button (224) or through irrigation fluid button (224) being depressed during robotic actuation. Energy breaker (510) prevents current from traveling proximally (e.g., to robot arm (16, 110) or irrigation fluid source (236). Energy breaker (510) prevents current from traveling distally to shaft assembly (214, 314, 414), articulatable section (216, 316), end effector (218, 318, 418), or to patient (P).

III. Examples of Combinations

The following examples relate to various non-exhaustive ways in which the teachings herein may be combined or applied. The following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A robotic surgical system, comprising: (a) a robotic arm; and (b) a surgical instrument configured to connect with the robotic arm and be inserted into a patient, the surgical instrument comprising: (i) a shaft assembly projecting distally from the robotic arm along a longitudinal axis, wherein the shaft assembly includes a fluid passageway, (ii) an end effector comprising: (A) an electrode configured to apply electrosurgical energy to tissue, and (B) at least one aperture in fluid communication with the fluid passageway, wherein the at least one aperture is configured to receive a fluid or a vacuum therethrough for irrigating the tissue or removing debris from the patient, and (iii) an articulatable section disposed between the shaft assembly and the end effector, wherein the articulatable section is configured to deflect the end effector between a straight configuration where the end effector extends along the longitudinal axis and an articulated configuration where the end effector is deflected from the longitudinal axis.

Example 2

The robotic surgical system of Example 1, wherein the articulatable section includes a flexible metallic feature configured to transmit the electrosurgical energy through the articulatable section in the straight configuration and the articulated configuration, wherein the flexible metallic feature is in electrical communication with the electrode.

Example 3

The robotic surgical system of Example 2, wherein the flexible metallic feature includes a flexible metallic helical member configured to transmit the electrosurgical energy to the electrode and provide strength to the articulatable section.

Example 4

The robotic surgical system of Example 3, wherein the articulatable section includes a flexible tube, wherein the flexible metallic helical member is at least partially embedded within the flexible tube.

Example 5

The robotic surgical system of any of Examples 3 through 4, wherein the flexible metallic helical member includes at least one of stainless steel, copper, or silver.

Example 6

The robotic surgical system of any of Examples 2 through 5, further comprising an intermediate metallic feature disposed between and electrically coupled with the electrode and the flexible metallic feature.

Example 7

The robotic surgical system of any of Examples 2 through 6, wherein the shaft assembly further comprises a metallic conduit configured to circumferentially surround at least a portion of the fluid passageway, wherein the metallic conduit is in electrical communication with the flexible metallic feature.

Example 8

The robotic surgical system of Example 7, wherein the metallic conduit and the flexible metallic feature each circumferentially surround different longitudinal portions of the fluid passageway.

Example 9

The robotic surgical system of any of Examples 1 through 8, wherein the electrode is positioned at a distal most tip of the end effector.

Example 10

The robotic surgical system of any of Examples 1 through 9, wherein the electrode includes a continuous metallic ring that is configured to apply monopolar electrosurgical energy to the tissue.

Example 11

The robotic surgical system of any of Examples 1 through 9, wherein the end effector includes a second electrode configured to coordinate with the electrode to apply bipolar electrosurgical energy to the tissue.

Example 12

The robotic surgical system of any of Examples 1 through 11, further comprising an energy breaker configured to prevent energizing the irrigation fluid by terminating a flow of current to the electrode in response to application of the irrigation fluid.

Example 13

The robotic surgical system of Example 12, wherein the energy breaker is configured to be activated manually by a user or automatically by the robotic surgical system.

Example 14

The robotic surgical system of Example 13, wherein the energy breaker includes at least one of a relay switch, a gate switch, a dome switch, a push button switch, or a toggle switch.

Example 15

The robotic surgical system of any of Examples 1 through 14, wherein the robotic arm includes a distal end, the robotic surgical system further comprising a tool driver operatively coupled with the distal end of the robotic arm, wherein the surgical instrument includes a tool drive adapter operatively coupled with the tool driver.

Example 16

The robotic surgical system of Example 15, the tool driver comprising: (i) a stage, and (ii) a carriage configured to move relative to the stage, wherein the carriage is configured to move the tool drive adapter from a non-engaged configuration to an engaged configuration.

Example 17

The robotic surgical system of any of Examples 1 through 16, wherein the at least one aperture further comprises a plurality of laterally extending apertures extending between the electrode and the articulation joint.

Example 18

The robotic surgical system of any of Examples 1 through 17, wherein the at least one aperture further comprises a distal aperture that extends through the electrode.

Example 19

The robotic surgical system of any of Examples 1 through 18, wherein the electrode is configured to denature and coagulate the tissue.

Example 20

The robotic surgical system of any of Examples 1 through 19, wherein surgical instrument is configured to simultaneously remove tissue and smoke from the patient through the fluid passageway.

Example 21

The robotic surgical system of any of Examples 1 through 20, wherein the articulatable section includes at least one cable configured to move the articulatable section between the straight configuration and the articulated configuration.

Example 22

The robotic surgical system of any of Examples 1 through 21, further comprising a second robotic arm.

Example 23

The robotic surgical system of any of Examples 1 through 22, wherein the debris includes smoke, wherein the robotic surgical system is configured to automatically apply the vacuum to evacuate the smoke from the patient.

Example 24

The robotic surgical system of any of Examples 1 through 23, wherein the robotic surgical system is configured to simultaneously apply both the vacuum to evacuate the debris from the patient and the electrosurgical energy to the tissue using the electrode.

Example 25

A surgical instrument comprising: (a) a shaft assembly extending distally along a longitudinal axis, wherein the shaft assembly includes a fluid passageway; (b) an end effector comprising: (i) an electrode configured to apply electrosurgical energy to tissue, and (ii) at least one aperture in fluid communication with the fluid passageway, wherein the aperture is configured to receive a fluid or a vacuum therethrough for irrigating the tissue or removing debris from the patient; and (c) an articulatable section disposed between the shaft assembly and the end effector, wherein the articulatable section is configured to deflect the end effector between a straight configuration where the end effector extends along the longitudinal axis and an articulated configuration where the end effector is deflected away from the longitudinal axis, wherein the articulatable section includes a flexible metallic feature configured to transmit the electrosurgical energy through the articulatable section to the electrode.

Example 26

The surgical instrument of Example 25, further comprising a body configured to couple with a robotic surgical system.

Example 27

A robotic surgical system, comprising: (a) a robotic arm; and (b) a surgical instrument configured to connect with the robotic arm and be inserted into a patient, the surgical instrument comprising: (i) a shaft assembly projecting distally from the robotic arm along a longitudinal axis, wherein the shaft assembly includes a fluid passageway, (ii) an end effector comprising: (A) an electrode configured to apply electrosurgical energy to tissue, and (B) at least one aperture in fluid communication with the fluid passageway, wherein the at least one aperture is configured to receive a fluid or a vacuum therethrough for irrigating the tissue or removing debris from the patient, and (iii) an energy breaker configured to prevent energizing the irrigation fluid by terminating a flow of current to the electrode in response to application of the irrigation fluid.

Example 28

The robotic surgical system of Example 27, wherein the energy breaker includes at least one of a relay switch, a gate switch, a dome switch, a push button switch, or a toggle switch.

Example 29

The robotic surgical system of any of Examples 27 through 28, further comprising an articulatable section disposed between the shaft assembly and the end effector, wherein the articulatable section is configured to deflect the end effector between a straight configuration where the end effector extends along the longitudinal axis and an articulated configuration where the end effector is deflected from the longitudinal axis.

Example 30

The robotic surgical system of any of Examples 27 through 29, wherein the surgical instrument does not articulate relative to the longitudinal axis.

IV. Miscellaneous

For clarity of disclosure, the terms "proximal" and "distal" are defined herein relative to a surgeon or other operator grasping a surgical instrument having a distal surgical end effector. The term "proximal" refers the position of an element closer to the surgeon or other operator and the term "distal" refers to the position of an element closer to the surgical end effector of the surgical instrument and further away from the surgeon or other operator.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components.

It should be understood that any of the versions of the instruments described herein may include various other features in addition to or in lieu of those described above. By way of example only, any of the devices herein may also include one or more of the various features disclosed in any of the various references that are incorporated by reference herein. Various suitable ways in which such teachings may be combined will be apparent to those skilled in the art.

While the examples herein are described mainly in the context of uterine manipulator instruments, it should be understood that various teachings herein may be readily applied to a variety of other types of devices. By way of example only, the various teachings herein may be readily applied to other types of surgical instruments including tissue graspers, tissue retrieval pouch deploying instruments, surgical staplers, surgical clip appliers, ultrasonic surgical instruments, etc. It should also be understood that the teachings herein may be readily applied to any of the instruments described in any of the references cited herein, such that the teachings herein may be readily combined with the teachings of any of the references cited herein in numerous ways. Other types of instruments into which the teachings herein may be incorporated will be apparent to those skilled in the art.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those skilled in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions or other disclosure material set forth herein will only be incorporated to the extent that no conflict arises between that incorporated material and the existing disclosure material.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A robotic surgical system, comprising:

(a) a robotic arm; and (b) a surgical instrument configured to connect with the robotic arm and be inserted into a patient, the surgical instrument comprising:

(i) a shaft assembly projecting distally from the robotic arm along a longitudinal axis, wherein the shaft assembly includes a fluid passageway and a metallic conduit, wherein the metallic conduit is configured to circumferentially surround at least a portion of the fluid passageway, (ii) an end effector comprising:

(A) an electrode configured to apply electrosurgical energy to tissue, and (B) at least one aperture in fluid communication with the fluid passageway, wherein the at least one aperture is configured to receive a fluid or a vacuum therethrough for irrigating the tissue or removing debris from the patient, and (iii) an articulatable section disposed between the shaft assembly and the end effector, wherein the articulatable section is configured to deflect the end effector between a straight configuration where the end effector extends along the longitudinal axis and an articulated configuration where the end effector is deflected from the longitudinal axis.

2. The robotic surgical system of claim 1, wherein the articulatable section includes a flexible metallic feature configured to transmit the electrosurgical energy through the articulatable section in the straight configuration and the articulated configuration, wherein the flexible metallic feature is in electrical communication with the electrode.

3. The robotic surgical system of claim 2, wherein the flexible metallic feature includes a flexible metallic helical member configured to transmit the electrosurgical energy to the electrode and provide strength to the articulatable section.

4. The robotic surgical system of claim 3, wherein the articulatable section includes a flexible tube, wherein the flexible metallic helical member is at least partially embedded within the flexible tube.

5. The robotic surgical system of claim 2, further comprising an intermediate metallic feature disposed between and electrically coupled with the electrode and the flexible metallic feature.

6. The robotic surgical system of claim 2, wherein the metallic conduit is in electrical communication with the flexible metallic feature.

7. The robotic surgical system of claim 6, wherein the metallic conduit and the flexible metallic feature each circumferentially surround different longitudinal portions of the fluid passageway.

8. The robotic surgical system of claim 1, wherein the electrode is positioned at a distal most tip of the end effector.

9. The robotic surgical system of claim 1, wherein the electrode includes a continuous metallic ring that is configured to apply monopolar electrosurgical energy to the tissue.

10. The robotic surgical system of claim 1, wherein the end effector includes a second electrode configured to coordinate with the electrode to apply bipolar electrosurgical energy to the tissue.

11. The robotic surgical system of claim 1, further comprising an energy breaker configured to prevent energizing the irrigation fluid by terminating a flow of current to the electrode in response to application of the irrigation fluid.

12. The robotic surgical system of claim 11, wherein the energy breaker is configured to be activated manually by a user or automatically by the robotic surgical system.

13. The robotic surgical system of claim 12, wherein the energy breaker includes at least one of a relay switch, a gate switch, a dome switch, a push button switch, or a toggle switch.

14. The robotic surgical system of claim 1, wherein the debris includes smoke, wherein the robotic surgical system is configured to automatically apply the vacuum to evacuate the smoke from the patient.

15. The robotic surgical system of claim 1, wherein the robotic surgical system is configured to simultaneously apply both the vacuum to evacuate the debris from the patient and the electrosurgical energy to the tissue using the electrode.

16. A surgical instrument comprising:
(a) a shaft assembly extending distally along a longitudinal axis, wherein the shaft assembly includes a fluid passageway and a metallic conduit, wherein the metallic conduit is configured to circumferentially surround at least a portion of the fluid passageway;
(b) an end effector comprising:
(i) an electrode configured to apply electrosurgical energy to tissue, and
(ii) at least one aperture in fluid communication with the fluid passageway, wherein the aperture is configured to receive a fluid or a vacuum therethrough for irrigating the tissue or removing debris from the patient; and
(c) an articulatable section disposed between the shaft assembly and the end effector, wherein the articulatable section is configured to deflect the end effector between a straight configuration where the end effector extends along the longitudinal axis and an articulated configuration where the end effector is deflected away from the longitudinal axis, wherein the articulatable section includes a flexible metallic feature configured to transmit the electrosurgical energy through the articulatable section to the electrode.

17. A robotic surgical system, comprising:
(a) a robotic arm; and
(b) a surgical instrument configured to connect with the robotic arm and be inserted into a patient, the surgical instrument comprising:

(i) a shaft assembly projecting distally from the robotic arm along a longitudinal axis, wherein the shaft assembly includes a fluid passageway,
(ii) an end effector comprising:
(A) an electrode configured to apply electrosurgical energy to tissue, and
(B) at least one aperture in fluid communication with the fluid passageway, wherein the at least one aperture is configured to receive a fluid or a vacuum therethrough for irrigating the tissue or removing debris from the patient,
(iii) an energy transfer system configured to communicate electrosurgical energy from a generator to the electrode,
(iv) an irrigation actuator configured to selectively move from an unactuated position to an actuated position, wherein the irrigation actuator in the unactuated position avoids applying an irrigation fluid through the at least one aperture, and wherein the irrigation actuator in the actuated position initiates the irrigation fluid through the at least one aperture, and
(v) an energy breaker operatively connected between the irrigation actuator and the energy transfer system, wherein the energy breaker is configured to move from a connected configuration to a disconnected configuration upon the irrigation actuator selectively moving from the unactuated position to the actuated position, wherein the energy breaker in the connected configuration electrically closes the energy transfer system to thereby allow communication of electrosurgical energy to the electrode with the irrigation actuator in the unactuated position, and wherein the energy breaker in the disconnected configuration electrically opens the energy transfer system to thereby prevent communication of electrosurgical energy to the electrode and further prevent energizing the irrigation fluid by terminating a flow of current to the electrode with the irrigation actuator in the actuated position.

18. The robotic surgical system of claim 17, wherein the energy breaker includes at least one of a relay switch, a gate switch, a dome switch, a push button switch, or a toggle switch.

19. The robotic surgical system of claim 17, further comprising an articulatable section disposed between the shaft assembly and the end effector, wherein the articulatable section is configured to deflect the end effector between a straight configuration where the end effector extends along the longitudinal axis and an articulated configuration where the end effector is deflected from the longitudinal axis.

20. The surgical instrument of claim 16, wherein the metallic conduit is in electrical communication with the flexible metallic feature.

* * * * *